(12) United States Patent
Forssmann et al.

(10) Patent No.: US 6,579,849 B2
(45) Date of Patent: *Jun. 17, 2003

(54) ANTIBIOTIC PEPTIDES FROM BOVINE MILK

(75) Inventors: Wolf-Georg Forssmann, Hannover (DE); Hans-Dieter Zucht, Hannover (DE); Manfred Raida, Heidelberg (DE); Knut Adermann, Hannover (DE); Hans-Jürgen Mägert, Hannover (DE)

(73) Assignee: HaemoPep Pharma GmbH, Hannover (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,203

(22) PCT Filed: Mar. 25, 1996

(86) PCT No.: PCT/EP96/01296
§ 371 (c)(1),
(2), (4) Date: Sep. 24, 1998

(87) PCT Pub. No.: WO97/35877
PCT Pub. Date: Oct. 2, 1997

(65) Prior Publication Data
US 2002/0025928 A1 Feb. 28, 2002

(51) Int. Cl.[7] ........................ A61K 38/00; A61K 38/16; C07K 14/00
(52) U.S. Cl. ................. 514/12; 514/2; 514/13; 530/300; 530/350; 530/324; 530/326; 530/360; 530/361; 435/213
(58) Field of Search ................. 530/300, 350, 530/324, 326, 360, 361; 514/12, 2, 13; 435/213

(56) References Cited

FOREIGN PATENT DOCUMENTS

DE 44 44 753 A1 6/1996

OTHER PUBLICATIONS

Brignon et al., "Complete Amino Acid Sequence of Bovine $\alpha_{S2}$–Casein" FEBS Letters, vol. 76(2), pp. 274–279, 1977.*
Brignon et al., "Premiers Elements De Structure Primaire Des Casines $\alpha_{S2}$ Bovines" FEBS Letters, vol. 71(1), pp. 111–116, 1976.*
Zucht et al, Casocidin–I: A Casein $\alpha_{S2}$ Derived Peptide Exhibits Antibacterial Activity FEBS Letters vol. 372, pp. 185–188, Sep. 1995.*
Zucht et al., FEBS Letters, "Casocidin–I: a casein–$\alpha_{S2}$ derives peptide exhibits antibacterial activity", pp. 185–188, 1995.
Zucht et al., The FASEB Journal, Abstracts, Experimental Biology 96™, Washington, D.C., 1996.
Chemical Abstracts, vol. 124, No. 3, Jan. 15, 1996.

* cited by examiner

Primary Examiner—Christopher S. F. Low
Assistant Examiner—Chih-Min Kam
(74) Attorney, Agent, or Firm—Jacobson Holman PLLC

(57) ABSTRACT

A peptide having the amino acid sequence

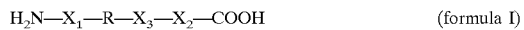

(formula I)

wherein
$X_1$ is either zero or
$X_1$ and/or $X_2$ are a residue representing at least five amino acid residues (symbolized in the one letter amino acid code), preferably naturally occurring amino acids,
with the proviso that
$X_1$ and/or $X_2$ contain at least one basic amino acid residue immediately followed by a hydrophobic amino acid residue and
$X_1$ and/or $X_2$ contain at least one glutamine residue.

17 Claims, 7 Drawing Sheets

SEQUENCE LISTING

<160> NUMBER OF SEQ ID NOS: 5

<210> SEQ ID NO 1
<211> LENGTH: 39
<212> TYPE: PRT
<213> ORGANISM: Bovine sp.

<400> SEQUENCE: 1

Lys Thr Lys Leu Thr Glu Glu Glu Lys Asn Arg Leu Asn Phe Leu Lys
 1               5                  10                  15

Lys Ile Ser Gln Arg Tyr Gln Lys Phe Ala Leu Pro Gln Tyr Leu Lys
                20                  25                  30

Thr Val Tyr Gln His Gln Lys
            35

```
<210> SEQ ID NO 2
<211> LENGTH: 38
<212> TYPE: PRT
<213> ORGANISM: Bovine sp.

<400> SEQUENCE: 2

Thr Lys Leu Thr Glu Glu Glu Lys Asn Arg Leu Asn Phe Leu Lys Lys
 1               5                  10                  15

Ile Ser Gln Arg Tyr Gln Lys Phe Ala Leu Pro Gln Tyr Leu Lys Thr
            20                  25                  30

Val Tyr Gln His Gln Lys
        35

<210> SEQ ID NO 3
<211> LENGTH: 31
<212> TYPE: PRT
<213> ORGANISM: Bovine sp.

<400> SEQUENCE: 3

Lys Asn Arg Leu Asn Phe Leu Lys Lys Ile Ser Gln Arg Tyr Gln Lys
 1               5                  10                  15

Phe Ala Leu Pro Gln Tyr Leu Lys Thr Val Tyr Gln His Gln Lys
            20                  25                  30

<210> SEQ ID NO 4
<211> LENGTH: 19
<212> TYPE: PRT
<213> ORGANISM: Bovine sp.

<400> SEQUENCE: 4

Arg Tyr Gln Lys Phe Ala Leu Pro Gln Tyr Leu Lys Thr Val Tyr Gln
 1               5                  10                  15

His Gln Lys

<210> SEQ ID NO 5
<211> LENGTH: 15
<212> TYPE: PRT
<213> ORGANISM: Bovine sp.

<400> SEQUENCE: 5

Lys Asn Arg Leu Asn Phe Leu Lys Lys Ile Ser Gln Arg Tyr Gln
 1               5                  10                  15
```

ANTIBIOTIC PEPTIDES FROM BOVINE MILK

This application is a 371 of PCT/EP96/01296 filed Mar. 25, 1996.

The present invention is concerned with peptides having the amino acid according to claim 1, fragments of the peptides obtainable by proteolytic cleavage, a medicament comprising a peptide of the invention, a process for the manufacturing of peptides of the invention, a method of treating by ad-ministering a peptide of the invention as well as methods of using the peptides of the invention.

Antimicrobial peptides are small peptide compounds which are capable to decrease the incidence of disease and could serve as modulators of a naturally occurring bacterial flora (Ganz T. et al., 1992, Med. Microbiol. Immunol. 181, 99–105; Eisenhauer P. B. et al., 1992, Infect. Immun. 60, 3556–3565; Oulette A. J. et al., 1992, FEBS Lett. 304, 146–148; Jones D. E. and Bevins C. L., 1993, FEBS Lett. 315, 187–192; Selstedt M. E. et al. (1992) J. Cell. Biol. 118, 929–936).

The fact that milk could influence micro-organisms is also well established (Wharton B. A. et al, 1994, Acta Paediatr. Jpn. 36, 579–584). Present factors thought to be responsible are lactoferrin (Bullen J. J. et al., 1972, Brit. J. Med. 1, 69–72; Baggiolini M. et al, 1970, J. Exp. Med. 13, 559–570), lysozyme (Fleming A., 1922, Proc. Roy. Soc., London, 93, 306–317, Jolles J. and Jolles P., 1968, Bull. Soc. Chim. Biol., Paris, 50, 2543–2551), lactoperoxidase (Cals M. M. et al., 1991, Eur. J. Biochem. 198, 733–739, Bullen J. J. et al., 1972, Brit. J. Med. 1, 69–72). Milk is a rich source of peptides mainly derived from proteolytic cleavage of proteins. Beyond a nutritive value several biological effects were described like immunomodulation, antithrombotic activities, opioid action or inhibition or mineral carriage (Meisel H. et al., 1989, Z. Ernährungswiss. 28, 267–278; Fiat A. M. and Jolles P., 1989, Mol. Cell. Biochem. 87, 5–30; Fiat A. M. et al., 1993, J. Dairy. Sci. 76, 301–310).

Casocidin-I is a peptide compound, a defined cleavage product from casein-alpha-s2, which is naturally occurring in bovine milk as it could be purified in authentic form (Zucht H. D., 1995, FEBS Lett. 372, 185–188). It has no counterpart in human milk since human milk does not contain any casein of the alpha-s2 type.

Surprisingly, the mild antibacterial effect found in milk could be enriched several orders of magnitude by the peptides of the invention. According to the invention a peptide with antibiotic effects show the amino acid sequence

$H_2N—X_1—R—X_2—COOH$ (formula I)

wherein
$X_1$ is either zero or
$X_1$ and/or $X_2$ are a residue representing at least five amino acid residues (symbolized in the one letter amino acid code) preferably naturally occurring amino acids,
with the proviso that
$X_1$ and/or $X_2$ contain at least one basic amino acid residue immediately followed by a hydrophobic amino acid residue and
$X_1$ and/or $X_2$ contain at least one glutamine residue.

Preferably, the distance of the hydrophobic residue and R should not exceed 7–10 amino acids.

Figure 1A:
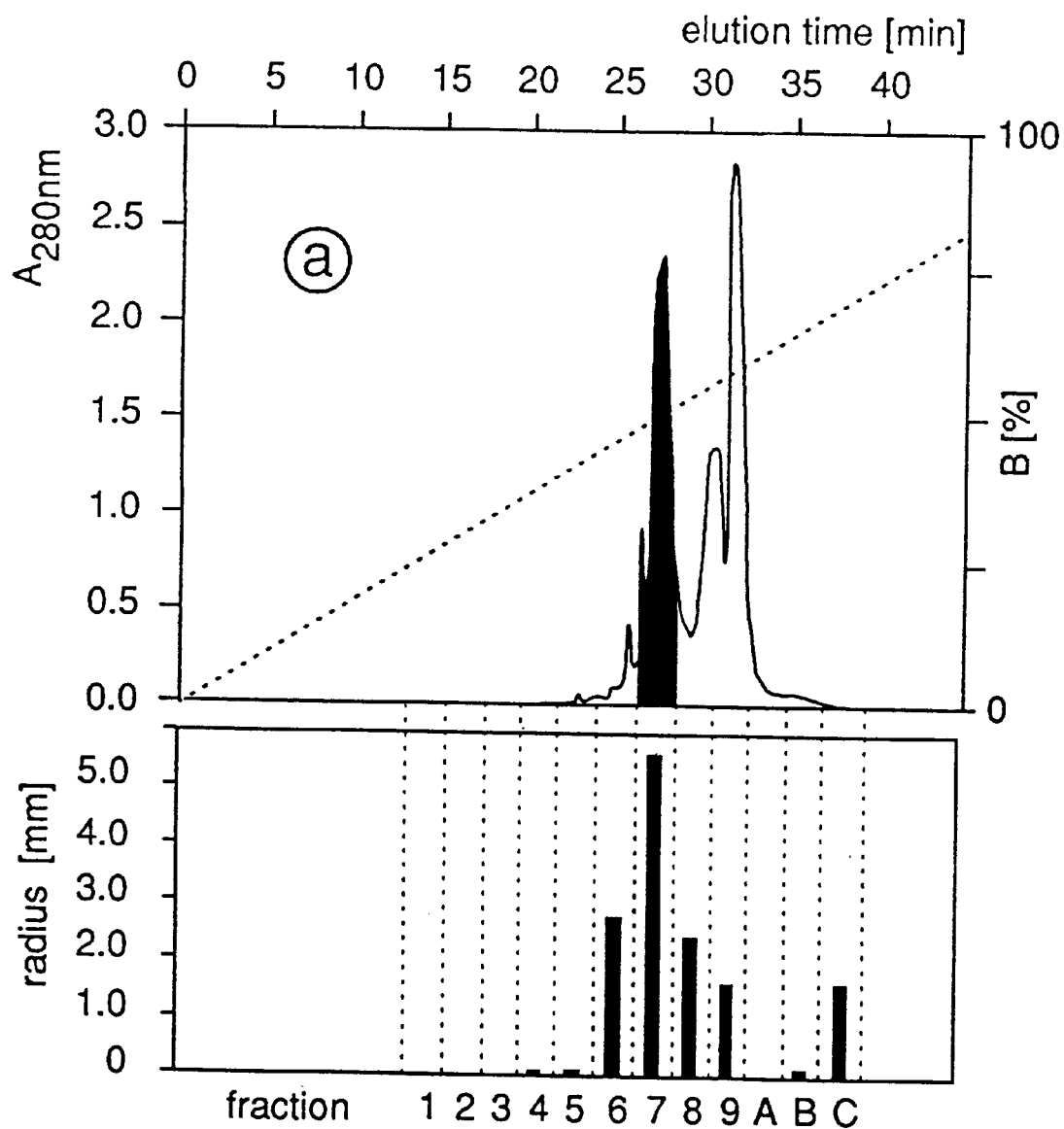
FIG. 1(a) provides graphs recording RP-C18 HPLC of the peptides eluted from a cation exchanger and growth inhibitory activity monitored with E. coli in a radial diffusion assay.
Figure 1B:
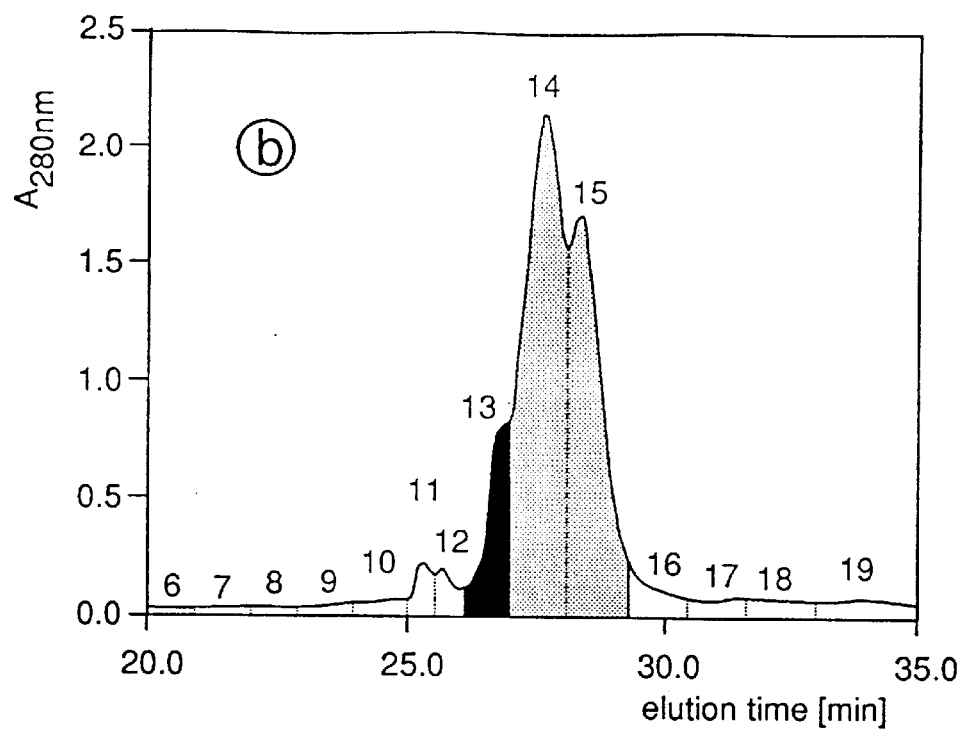
FIG. 1(b) is a graph of RP-C18 HPLC rechromatography of the most active fraction.
Figure 1C:
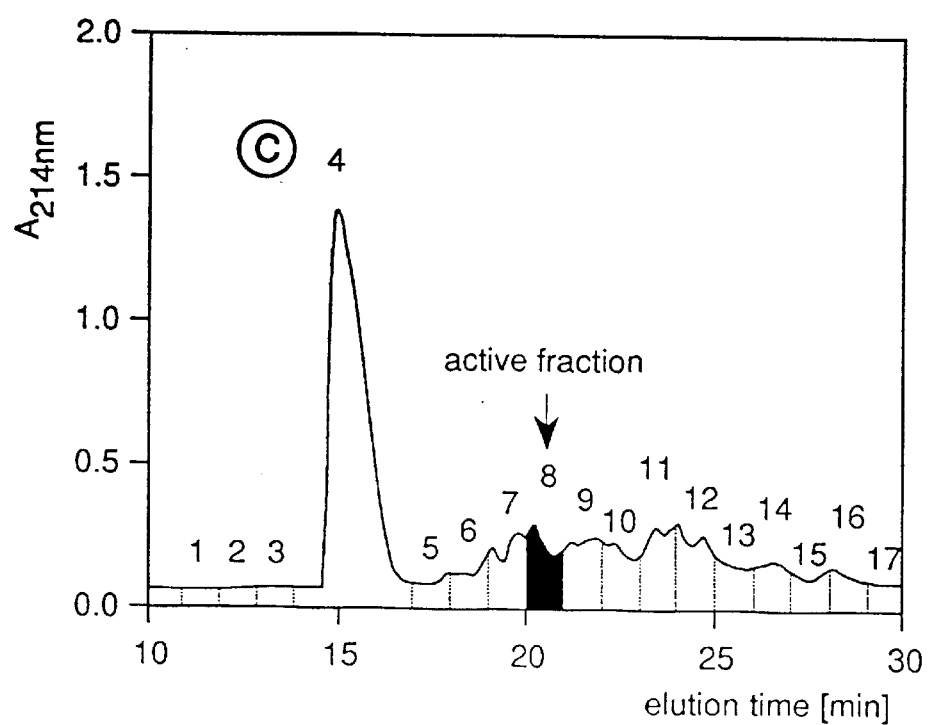
FIG. 1(c) graphs RP-C4 HPLC rechromatography of fraction 13.
Figure 1D:
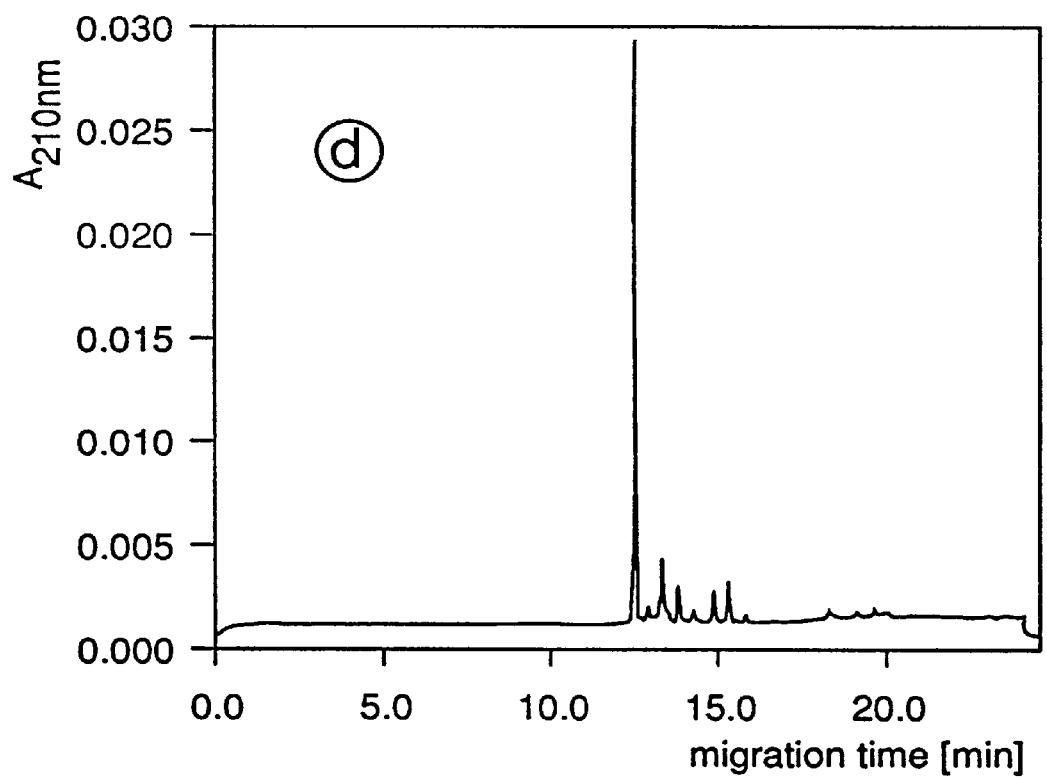
FIG. 1(d) graphs CZE analysis of the purification product Casocidin-I.

It has now been found that these peptides could kill a broad range of microorganisms with a preference of microorganisms not naturally present in the normal intestinal flora. Surprisingly, the peptides of the invention show activity also against eukaryotic organisms such as fungi but do not effect other eukaryotic cells as for example HT 29 cells. The peptides of the invention are therapeutical tools for treating diseases caused by pathogenic eukaryots, for example, protists which are only present in the adult cattle intestine and that of man respectively.

In a preferred embodiment the peptide of the invention has a structure wherein
$X_1$ represents $—X_m—K—B—X_n—$ wherein
X is any amino acid residue having at least one Q,
B is any hydrophobic amino acid residue;
m=0–40, n=0–8 and
$X_2$ is Q.

A further preferred embodiment of the peptide of the invention is a structure wherein
$X_1$ is zero or represents Q,
$X_2$ represents $—X_n—K—B—X_m—$,
X, B, m and n having the same meaning as defined above.

A further preferred embodiment of the present invention is a peptide having a structure wherein
$X_1$ represents $—X_m—K—B—X_n—$ and
$X_2$ represents $—X_n—K—B—X_m$,
X, B, m, and n have the same meanings as defined above.

It is understood by the skilled person that not only amino acids naturally occurring can be used in effective peptides. Therefore, the amino acids in the chain forming the peptides can be modified in order to match valuable properties for respective use. For example, it is possible to use mixtures of D- and/or L-amino acids in the amino acid sequence of the peptides of the invention in order to modify the pharmaceutical effects.

Furthermore, there may be introduced modification in the side chains of the peptide backbone of the amino acid sequence. For example, it is possible to introduce sugar moieties at suitable positions, for example, asparagine. Glycosylation modifies affinity of the peptides or its solubility. It may also be useful to phophorylate amino acids of the peptide of the invention. It may also be useful to modified amino acid side chains in order to modify the hydrophobicity or hydrophilicity of the peptide. For example, if the peptide is used in a pharmaceutical composition which is designed for topical application it may be advantageous to modify the peptide that it more easily penetrates the skin in order to develop its activity also in deeper layers of the skin. On the other hand if only a surface treatment is needed the properties of the peptide could be modified in so far as it is not penetrating too far into the deeper layers of the skin.

A further modification may occur at the N-terminal or C-terminal end of the peptide. The N-terminal end may be modified with electrophilic agents. For example, the N-terminal amino group may be alkylated, acylated, cleaved off or protected. The N-terminal end may be protected with labile chemical groups which are cleaved off during the use of the peptide. The C-terminal end of the peptides can be modified with nucleophilic reagents in order to attack the carbonyl group of the carboxyl and the C-terminal end may be modified, for example by amidation, esterification and the like.

It is possible to obtain peptides by proteolytic cleavage of the peptides of the invention. Such fragments which fall into the scope of the invention must show antifungal activity after protease treatment. Suitable proteases for obtaining fragments from the peptides of the invention are endo-proteinases like trypsin, subtilisin, thermolysin and endo-proteinase LYS-C.

Preferably, the peptide of the invention consists of a domain —RYQ-. However, for example, a tetrapeptide with the motif QRYQ alone is not sufficient to gain antimicrobial properties.

A further preferred structure on both sides of this core motif —RYQ- is the occurrence of one or more basic residues immediately followed by a hydrophobic amino acid residue. The specificity of the peptides of the invention can be modulated by composition of the residues flanking the core region —RYQ- so that the detailed antimicrobial spectrum of the peptide of the invention could be fine tuned by means of modulating residues around the core motif.

Within the side chain one or more glutamine residues seem to be of some relevance since the preferred peptide casocidin-I (casocidin 1–39) contains high an amount of glutamine residues. On the other side the glutamine residues alone do not promote the antimicrobial effect as casein-alpha-s2–80–120 shows a very similar glutamine pattern but does not exhibit any antibacterial effects.

Specifically preferred peptides according to the inventions are those as follows:

Casocidin-I

KTKLLTEEEKNRLNFLKKISQRYQK-FALPQYLKTVYQHQK (SEQ ID NO:1) (Casocidin 1–39)

TKITEEEKNRLNFLKKISQRYQK-FALPQYLKTVYQHQK (SEQ ID NO: 2) (Casocidin 2–39)

KNRLNFLKKISQRYQKFALPQYLKTVYQHQK (SEQ ID NO: 3) (Casocidin 9–39)

RYQKFALPQYLKTVYQHQK (SEQ ID NO: 4) (Casocidin 21–39)

KNRLNFLKKISQRYQ (SEQ ID NO: 5) (Casocidin 9–23).

As the skilled person understand also this very specific peptides can be modified according to the strategies outlined above discussing the general aspects of the invention.

According to the invention the process for the manufacturing of a peptide according to the invention comprises the steps of

- treating bovine milk with acetic acid and calcium sulfate,
- heating the mixture obtained
- removing the precipitate and isolating the supernatant,
- treating the supernatant with a cation-exchanger resin for binding of basic peptides, washing the resin optionally with a urea solution to remove non specifically bound material,
- isolating the resin having peptides bound to it,
- elution of peptides bound to the resin and further purification with chromatographic operations,
- optionally followed by fragmentation, e.g. by digestion with proteases.

The precise conditions are exemplified in the working examples of the specification herein below. The biological activity of the peptides of the invention show a broad range specificity against grampositive and gramnegative bacteria. They are also capable to inhibit the growth of fungi exemplified on Rhodotorula rubra. Intestinal cells were not killed. This shows that they are specifically effective against the pathogene but not against the host. Preferably, the activity is pronounced in low ion strength media in the absence of high amounts of calcium. It is preferred to administer the peptide of the invention in a hypotonic medium in the presence of calcium complexing agents such as citrate, phosphate, EGTA in order to facilitate its activity. The mechanism of action may be due to the membrane permeabilizing effect of the peptide depending on the dosage of the peptides of the invention.

The peptides of the invention can be used for formulating a medicament for treating diseases which are caused by bacteria or fungi. The medicament optionally contains further active compounds or carrier materials and or adjuvants. In a preferred embodiment of the present invention the medicament of the invention is formulated for topical administration or administration on mucosa such as the mucosa of mouth and vagina. Because of its antifungal potency the medicament of the present invention is preferably useable for treating fungal diseases and or treatment of diseases which are caused by eukaryotic organisms such as tricho-monades, for example in vagina, or organisms such as filaria or plasmodium.

The peptide of the invention preferably casocidin-I can be administered in the form of an oral dosage unit together with fillers which are pharmaceutically acceptable. It can be used in liquid preparations or in a dry preparation with lyophilized peptide. The typical dosage would be in the range of 1 $\mu$g/ml up to 250 $\mu$g/ml of the medicament. Casocidin-I keeps its potency when lyophilized and can be stored at room temperature in this form. It allows long term storage with reconstitution with an appropriate low ion strength buffer, for example, 25 mOsm prior to use. A supplementation with pharmaceutically acceptable agents capable to complex calcium like citrate (about 5–250 mM), phosphate (5–150 mM) or EGTA (1 mM) support the antimicrobial effect of the drug.

If antimicrobial diseases of the skin have to be treated the formulation preferably is in the form of an ointment. The concentration range of the drug in such a formulation is comparable to the above mentioned range of 0,1 ng/ml to 1 mg/ml, preferably 1 $\mu$g/ml to 250 $\mu$g/ml. The dosis can be adjusted obeying the rules of the art as can readily understood by the skilled person.

The peptides of the invention can be used for therapy of diseases such as diarrhoea, diseases caused by a change of the microbiological properties or conditions in the intestine, the mucosa of the vagina or the mouth, diseases of the skin and diseases caused by fungi.

The peptide of the invention can be used as preservative of food or perishable goods or as adjuvant for fermentation processes.

FIG. 1

Purification of casocidin-I: (a) RP-C18 HPLC of the peptides eluted from the cation exchanger. The growth inhibitory activity was monitored with *E. coli* in the radial diffusion assay. (b) RP-C18 HPLC rechromatography of the most active fraction. (c) RP-C4 HPLC rechromatography of fraction 13. (d) CZE analysis of the purification product casocidin-I.

FIG. 2

Effect of casocidin-I on the CFU of E. coli BL21 depending on incubation time and dosage. The picture shows various plates with bacterial colonies.

FIG. 3

Dose response curves of casocidin-I with diverse microorganisms in the preincubation experiment (determination of CFU).

FIG. 4

Radial diffusion experiment, indicating the antimicrobial activity of casocidin-I.

FIG. 5

Release of intracellular enzymes beta-lactamase and beta-galactosidase indicating the effect of casocidin-I.

The purification of casocidin-I out of bovine milk is exemplified as follows.

Grade A bovine milk is to be used. In order to denature most of the high molecular weight proteins, the milk must be initially treated by boiling for 5 min and acidifying with 10% (v/v) acetic acid. Additionally, 1 g/l calcium chloride ($CaCl_2 \cdot 2\ H_2O$) is added to precipitate calcium-dependent phosphoproteins. After centrifugation (15 min, 3,500×g, and 4° C.) the resulting supernatant is collected, diluted with 4 volumes of water and incubated with a strong cation exchange resin (Parcomer, 20 µm, Biotek, Heidelberg, Germany).

The resin is washed with 5 M urea in 5 mM phosphate buffer (pH 3.0) and with an excess of water. To elute bound peptides the resin is treated with 1 M NaCl in 5 mM phosphate buffer (pH 3.0) at room temperature. The eluate is centrifuged (5 min, 1,000×g, RT) to remove residual resin particles.

Figure 2:
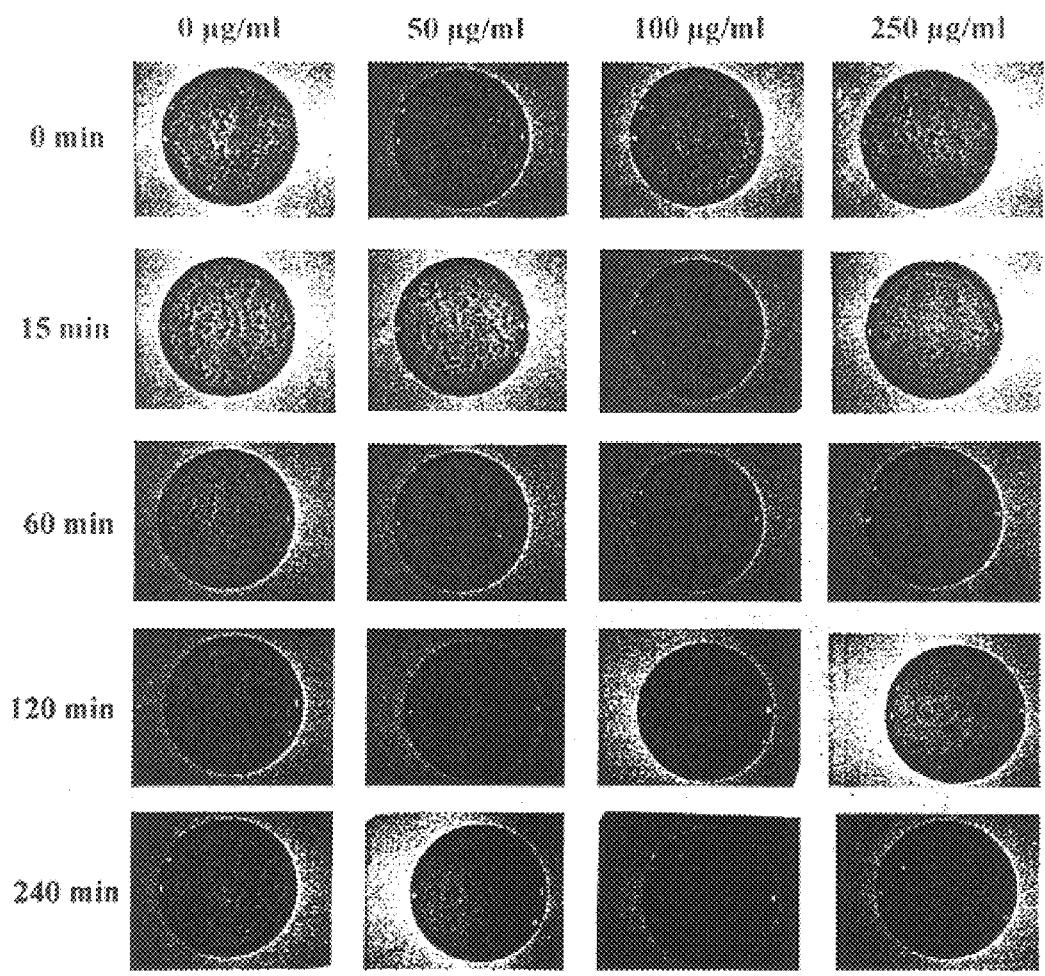
FIG. 2 provides pictures showing various plates with bacterial colonies, illustrating the effect of Casocidin-I on the CFU of E. coli BL21 depending on incubation time and dosage.

The HPLC purification steps were performed on Parcosil-$C_{18}$ (1 cm×12.5 cm, 100 Å, 5 µm) and Parcosil-$C_4$ (0.4 cm×12.5 cm, 300 Å, 5 µm) reversed phase columns (Biotek, Heidelberg, Germany). After equilibration with 0.1% trifluoroacetate (TFA), peptides are eluted by linearly increasing the amount of solvent B (acetonitrile with 0.1% TFA). For the first separation step a Parcosil $C_{18}$ RP column (1 cm×12.5 cm, 100 Å, 5 µm) is used with the following gradient: 0–50 min, 0–80% B. The bactericidal activity of an aliquot were monitored with the radial diffusion assay and the maximum activity was pooled. The second step of purification was performed with the same RP-$C_{18}$ column using a less steep gradient (gradient 2:0–5 min, 0–15% B; 5–65 min, 15–80% B) (FIG. 2). In the third step of purification, the antibiotic activity of fraction 13 could be recovered by RP-$C_4$ HPLC using the following gradient (0–5 min, 0–15% B; 5–65 min, 15–80% B). Fraction 8 contains casocidin-I with a relative high purity. The purification is illustrated in FIGS. 1 a–d.

The peptide analysis revealed the following structure of casocidin-I:

KTRLTEEEKNRLNFLKKJSQRYQK-FALPQYLKTVYQHQK (SEQ ID NO: 1)

Synthesis of Casocidin-I

Chemical synthesis of peptides was carried out as described elsewhere (Atherton E. and Sheppard R. C., 1989, Solid phase peptide synthesis, IRL Press, Oxford; Jones, J., 1991, The chemical synthesis of peptides, Clarendon Press, Oxford). The purification was performed on a Vydac RP-$C_{18}$ column (MZ-Analysentechnik, Mainz, Germany, 10 µm, 300 Å, 2 cm×25 cm) with 0.06% TFA/acetonitrile/water at a flow rate of 10 ml/min. The purity was controlled by means of HPLC and mass spectrometry.

Antimicrobial Assays

Bacteria

E. coli Xl1 blue is a commercial strain distributed by Stratagene (USA). E. coli BL 21 (DE3) was a gift from A. Ebneth (Medical School Hannover, Dept. of Biophysics). Staphylococcus carnosus T300 was a gift from F. Goetz (Freiburg). Rhodotorula rubra, Staph. epidermidis is a clinical isolate from I. Zimmer and M. Weimann (laboratory of Clinical Medicine, Hannover). All other bacteria were purchased at Deutsche Sammlung von Mikroorganismen und Zellkulturen GmbH (DSM, Braunschweig, Germany). All bacteria were routinely cultured on LB-Broth (10 g/l caseinhydroly-sate, 5 g/l yeast extract, 5 g/l NaCl, pH 7.4).

Preincubation Experiment

Exponentially grown bacteria with a density corresponding to an $A_{600}$ of 0.4 to 0.6, were initially diluted $1:10^5$ in 10 mM phosphate buffer (Na—P, pH 7.2) or phosphate buffered saline (PBS, pH 7.4) and incubated at 37° C. for 120 min in Na—P or PBS supplemented with different concentrations of peptides. After this period the reaction mixtures were diluted 1:10 and 1:100 in the same buffer and plated on LB-Agar to determine the colony forming units (CFU). The plating were done in triplets. The colonies were counted with a colony counter (Darkfield, Quebec, Canada).

Figure 3:
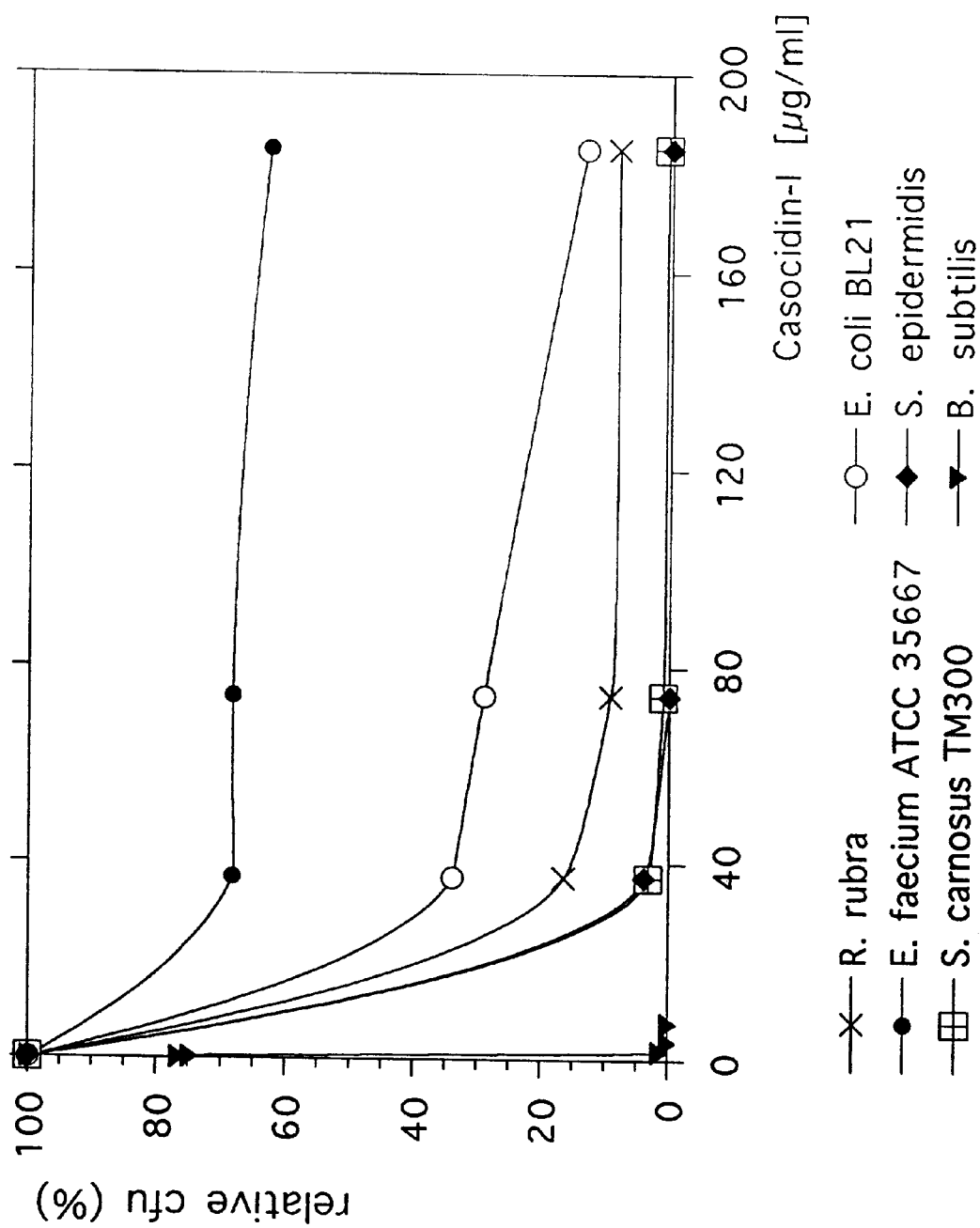
FIG. 3 graphs dose response curves of Casocidin-I with diverse microorganisms in a preincubation experiment (determination of CFU).

An example for the depletion of viable bacteria gives FIG. 2 showing that a time dependent killing of the bacteria during incubation occurs. Further results of preincubation experiments are summarized in FIG. 3. The interpolation of the date gives the following order of sensitivity of the used strains B. subtilis>S. carnosus=S. epidermidis>Rhodotorula >>E. coli>Enterococcus faecium ATCC 35667. The concentration necessary to reduce the colony forming units (CFU) to 50% of the initial CFU ranges from 180 µg/ml (E. faecium) over 20 µg/ml (E. coli, S. carnosus, R. rubra) to 1 µg/ml for B. subtilis indicating a potent inhibitory effect of the used peptide.

Radial Diffusion Experiment

Figure 4:
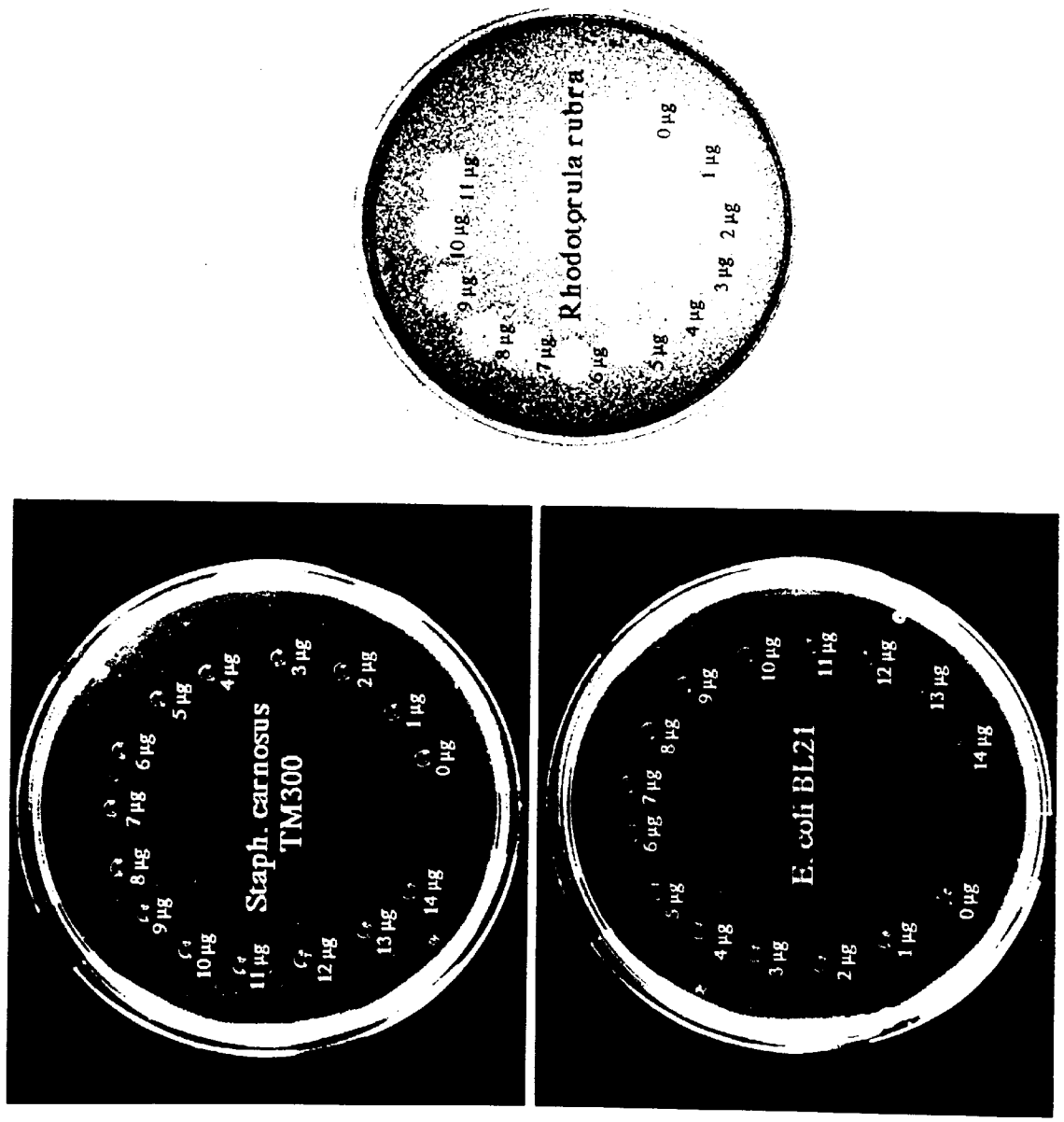
FIG. 4 provides pictures of plates resulting from a radial diffusion experiment, indicating the antimicrobial activity of Casocidin-I.

The radial diffusion assay performed as described in (Lehrer R. I. et al., 1991, J. Immun. Meth. 137, 167–173) with slight modifications. Bacteria were grown to a final absorbance at 580 nm of 0.2 (appr. $2 \times 10^{10}$/ml). The agarose layer contained 30 mg/100 ml tryptic soy broth (TSB, Sigma chemicals, Germany) in 10 mM sodiumphosphate 10 mM pH 7.2 with 0.02% Tween® 20 and 0.6% agarose without EEO (Serva, Heidelberg, Germany). One ml of the bacteria suspension was added to 50 ml agarose at 50° C. and the plates were poured immediately. Afterwards the plates were incubated at 4° C. to harden the agarose. The bacteria were incubated for 10 hours at 37° C. with the peptide substrate applied into holes of 3 mm diameter in the agarose layer. In some cases the plates were first fixed with 0.1% glutardialdehyde and afterwards stained with Giemsa stain (Merck, Darmstadt, Germany) diluted in 10 mM Tris-HCl pH 7.2 and washed with an excess of the same Tris Buffer. Using Rhodotorula rubra the medium contained 0.8% low melting point agarose (Sigma, Germany), 0.5 g/100 ml TSB and 20 mM TRIS-HCl pH 7.5. The yeast was added after an equilibration of the medium at 37° C. and poured into the plates. The incubation was performed for 10 h at 30° C. The inhibitory influence of casocidin-I shows FIG. 4.

Influence of Medium Strength and Calcium Ions

To determine the minimal inhibitory concentration of casocidin-I under the influence of the medium strength or in the presence of bivalent cations, a dilution assay was performed in 96-well cell culture clusters. After diluting the peptide in 50 μl medium (tryptic soy broth, Sigma, Germany) with adjusted pH 7.2, ion concentrations or medium strength on one plate, the same amount of medium with appr. 2–4*10³ bacteria in 50 μl medium were added to the diluted samples. The incubations were done overnight at 37° C. The minimal inhibitory concentration was manually read using a microscope.

TABLE

Example of the effect of the medium strength and bivalent cations on *S. carnosus*

| Medium strength | 1 | 0.5 | 0.2 | 0.1 | 0.05 | 0.02 |
|---|---|---|---|---|---|---|
| MIC μg/ml | no | 25 | 3.3 | 3.3 | 1.7 | 0.6 |

| bivalent Cation | 2.5 mM Mg | 10 mM Mg | 2.5 mM Ca | 2.5 mM Mn |
|---|---|---|---|---|
| MIC μg/ml | 20 | 100 | no | no |

Influence of casocidin on cell lines

HT 29 (human colon carcinoma) cells were grown as monolayers at 37° C. in RPMI 1640 medium (Gibco, Germany) containing 2 mM L-glutamine, 100 U/ml penicillin, 0.1 mg/ml streptomycin and 10% heat inactivated fetal calf serum in 5% $CO_2$ on 24-well tissue culture clusters (Nunc, Germany) by loading of a suspension of 5*10⁵ cells/ml. To determine the cytotoxic effect of casocidin-I, HT 29 cells were propagated in tissue culture clusters were incubated with different concentrations of casocidin-I (from 1 μg/ml to 100 μg/ml) for up to 24 h at 37°. The experiments show no cytotoxic effects to this intestinal cell line.

Determination of the Membrane Permeabilization

Figure 5:
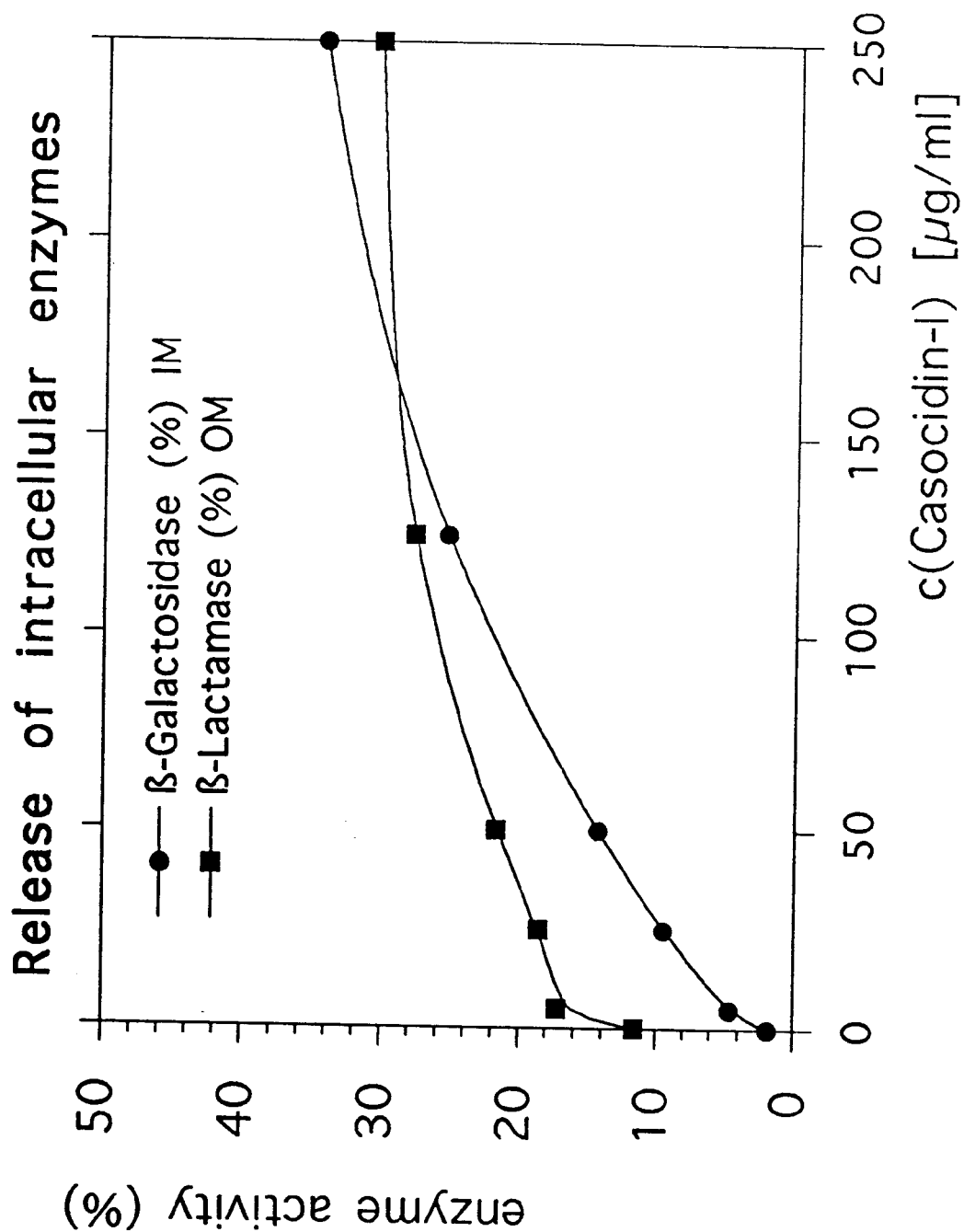
FIG. 5 graphs the release of intracellular enzymes beta-lactamase and beta-galactosidase indicating the effect of Casocidin-I.

To determine the mechanism of action of casocidin-I which is a membrane permeabilizing effect we determined the release of intracellular enzymes beta-galactosidase and beta-lactamase from *E. coli* transformed with the plasmid pUC18 (FIG. 5). The beta-galactosidase indicated the degree of the permeabilization of the inner membrane (IM) of *E. coli*. The permeabilization of the outer membrane was monitored by determination of released beta-Lactamase (plasmid coded) mainly present in the periplasmatic space.

To measure the relative release of beta-galactosidase a suspension of *E. coli* grown overnight in LB medium was washed once in phosphate buffer (10 mM, pH 7.0). Afterwards the bacteria were resuspended to a final density of app. 0.5 $A_{600}$. Peptide fractions were lyophilized in 1.5 ml tubes in a speed vac concentrator and solved in 40 μl phosphate buffer. To the peptide solution a volume of 200 μl bacterial suspension was added and the incubation was performed at 37° C. for 30 min. As a control, to determine the maximum of the enzyme release, bacteria were disrupted by ultrasonic treatment (about 100 joules in 10 sec). The samples were afterwards centrifuged for 5 min at 15,000×g at 4° C. and the supernatant immediately removed from the sediment. To detect the beta-galactosidase activity an amount of 40 μl lysate was mixed with 460 μl of the detection reagent (60 mM $Na_2HPO_4$, 400 mM $NaH_2PO_4$, 10 mM KCl, 1 mM $MgSO_4$, 50 mM beta-mercaptoethanol, 0.89 mg/ml o-nitro phenyl galactoside ONPG) and incubated at 37° C. for 45 min. The absorbance of the samples at 405 nm was measured and the increase of each absorbance was normalized to the sonified sample assuming enzymatic release of 100%.

To detect the release of beta-lactamase the supernatants of *E. coli* were prepared as described for the beta-galactosidase. As washing buffer PBS was used. To monitor the beta-lactamase activity an amount of 50 μl. supernatant was mixed with 50 μM PADAC (Calbiochem, USA) in 10 mM Na—P pH 7.2. The samples were incubated for 45 min at 37° C. in the dark and the absorbance was measured at a wavelength of 700 nm and the normalization was done with the results gained with sonified samples.

Peptide Analysis

Amino acid sequence determinations were carried out automatically on an Applied Biosystems 473 A gas phase sequencer (Applied Biosystems Div. of Perkin Elmer, Weiterstadt, Germany). Capillary zone electrophoresis (CZE) was performed with a 50 cm uncoated capillary of fused silica on the CZE system model P/ACE 2100 (Beckmann, München, Germany). The running buffer used was 100 mM $NaH_2PO_4$, pH 2.5 containing 0.02% hydroxypropyl methyl cellulose. After injection of 60 nl sample, the separation was carried out with a constant current of 120 μA. Mass spectrometric analysis (MS) was performed on a triple-stage quadrupole electrospray mass spectrometer Sciex API III (Perkin Elmer, Ueberlingen, Germany) equipped with an articulated ion-spray source operation at atmospheric pressure. The samples were diluted in 50% acetonitrile, 0.2% acetic acid prior to injection. Mass spectra were recorded in positive ion mode.

What is claimed is:

1. An isolated peptide consisting of an amino acid sequence selected from the group consisting of:
   KTKLTEEEKNRLNFLKKISQRYQK-FALPQYLKTVYQHQK (SEQ ID NO:1) (Casocidin 1–39),
   TKLTEEEKNRLNFLKKISQRYQK-FALPQYLKTVYQHQK (SEQ ID NO:2) (Casocidin 2–39),
   KNRLNFLKKJSQRYQKFALPQYLKTVYQHQK (SEQ ID NO:3) (Casocidin 9–39),
   RYQKFALPQYLKTVYQHQK (SEQ ID NO:4) (Casocidin 21–39), and
   KNRLNFLKKISQRYQ (SEQ ID NO:5) (Casocidin 9–23).

2. A physiologically compatible antimicrobial composition comprising at least one isolated peptide according to claim 1, in combination with a physiologically acceptable carrier.

3. The composition of claim 2 in liquid form.

4. The composition of claim 2 in dry form.

5. The composition of claim 2 in the form of an oral dosage unit.

6. The composition of claim 4 wherein the peptide is lyophilized.

7. The composition of claim 2 in ointment form suitable for applying topically or to mucosa.

8. The composition of claim 2 wherein the peptide is lyophilized.

9. The composition of claim 2 in a formulation for topical administration or mucosal administration.

10. The composition of claim 3 wherein the peptide is present at an amount of 0.1 ng–1 mg per ml of the composition.

11. The composition of claim 3 wherein the peptide is present at an amount of 1–250 µg per ml of the composition.

12. The composition of claim 2 further comprising a physiologically compatible calcium complexing agent.

13. A process of making a peptide comprising the steps of:

treating bovine milk with acetic acid and calcium sulfate to form a mixture, heating the mixture to form a precipitate and a supernatant, removing the precipitate from the supernatant, treating the supernatant with a cation-exchanger resin that specifically binds to basic peptides present in the supernatant, followed by optionally washing the resin with a urea solution to remove non-specifically bound material, isolating the resin having peptides bound to it, eluting from the resin the bound peptides, and purifying the eluted peptides by chromatographic procedure, wherein the peptide consists of an amino acid sequence selected from the group consisting of:

KTKLTEEERNRLNFLKKISQRYQKFALPQYLKTVYQHQK (SEQ ID NO:1) (Casocidin 1–39)

TKLTEEEKNRLNFLKKISQRYQKFALPQYLKTVYQHQK (SEQ ID NO:2) (Casocidin 2–39),

KNRLNFLKKISQRYQKFALPQYLKTVYQHQK (SEQ ID NO:3) (Casocidin 9–39),

RYQKFALPQYLKTVYQHQK (SEQ ID NO:4) (Casocidin 21–39), and

KNRLNFLKKISQRYQ (SEQ ID NO:5) (Casocidin 9–23).

14. The process of claim 13, further comprising the step of fragmenting the purified proteins by digesting with proteases.

15. A method of making a composition comprising the steps of combining a physiologically acceptable carrier with at least one peptide, wherein the at least one peptide consists of an amino acid sequence selected from the group consisting of:

KTKLTEEEKNRLNFLKKISQRYQKFALPQYLKTVYQHQK (SEQ ID NO:1) (Casocidin 1–39),

TKLTEEEKNRLNFLKKISQRYQKFALPQYLKTVYQHQK (SEQ ID NO:2) (Casocidin 2–39),

KNRLNFLKKISQRYQKFALPQYLKTVYQIIQK (SEQ ID NO:3) (Casocidin 9–39),

RYQKFALPQYLKTVYQHQK (SEQ ID NO:4) (Casocidin 21–39), and

KNRLNFLKKISQRYQ (SEQ ID NO:5) (Casocidin 9–23).

16. The method of claim 15 wherein the at least one peptide is lyophilized.

17. The method of claim 16, further comprising the step of reconstituting the lyophilized peptide.

* * * * *